United States Patent [19]

Shen

[11] 4,382,439

[45] May 10, 1983

[54] THUMB SPICA

[76] Inventor: C. Anthony Shen, 13800 Arizona St., Ste. 101, Westminster, Calif. 92683

[21] Appl. No.: 265,974

[22] Filed: May 21, 1981

[51] Int. Cl.³ .............................................. A61F 5/10
[52] U.S. Cl. .................................... 128/77; 128/89 R
[58] Field of Search ..................... 128/77, 87 R, 87 A, 128/90, 89 R, 94, 132; 273/189 R, 189 A

[56] References Cited

U.S. PATENT DOCUMENTS

| 1,471,948 | 10/1923 | Cox et al. | 128/89 R |
| 2,477,126 | 7/1949 | Hartmann | 128/90 X |
| 3,815,588 | 6/1974 | Klausner | 128/77 |
| 3,938,509 | 2/1976 | Barber | 128/77 |
| 4,190,902 | 3/1980 | Rhee | 128/87 R |
| 4,214,579 | 7/1980 | Ford | 128/77 X |

FOREIGN PATENT DOCUMENTS 346649  7/1960  Switzerland ..................... 128/87 R Primary Examiner—John D. Yasko
Attorney, Agent, or Firm—Knobbe, Martens, Olson, Hubbard & Bear

[57] ABSTRACT

A device for immobilizing the thumb, hand and wrist of an individual is a shell formed of an integral piece of semi-rigid material having portions shaped to receive the upper forearm, hand and thumb. The device is easily slipped on and off by means of expansion of a longitudinal opening which bifurcates the upper side of the device. The bottom and top sides of a region of the forearm portion are flat to prevent rotation of the individual's forearm within the device. The forearm portion is also shaped to accommodate the protrusion of an individual's ulnar bone on the upper side of the wrist. The diameter of the thumb portion is easily adjustable.

13 Claims, 5 Drawing Figures

THUMB SPICA

BACKGROUND OF THE INVENTION

The invention is generally related to devices for immobilizing an individual's thumb, hand and wrist and specifically, to those devices which can be easily slipped on and off the individual.

Plaster casts and various types of braces and splints are well known for immobilizing an individual's thumb, wrist and hand that has suffered a fracture, sprain or the like. Devices such as the plaster cast are difficult to remove and once removed cannot be reused.

Other devices such as wooden splints are not intended to be removed during use. Braces, such as those made of elastomeric fabric, while readily removable, do not provide optimum immobilization.

Recently, efforts have been made to produce a device which can be easily slipped on and off the individual and yet provides proper immobilization. One such device consists of a polyethylene body laminated to an inner foam liner. The upper side of the device is bifurcated by a longitudinal opening. The device is easily slipped on and off because the polyethylene allows the opening to expand when required. The device is secured to the patient's arm by buckling laterally spaced straps.

While this device solves some of the problems of past devices, it has several disadvantages. Some of these disadvantages are that the portion of the device which holds the thumb cannot be adjusted in size, the device does not adequately prevent rotation of an individual's forearm therein and the device does not provide for an individual's distal ulnar prominence, i.e., the natural protrusion of an individual's ulnar bone proximal the wrist on the upper side of the forearm opposite the thumb. Moreover, the padding of the device prevents it from securely immobilizing the individual's thumb, wrist and hand from being easily custom fit.

SUMMARY OF THE INVENTION

The present invention obviates the above described disadvantages of prior devices. The novel device is particularly adapted for temporary immobilization of suspected fractures of the thumb, hand and wrist for reexamination by x-ray and immobilization of thumb and wrist sprains and other soft tissue trauma of the thumb, hand and wrist.

The inventive device is a unitary open-ended hollow body of semi-rigid material having forearm, hand and thumb portions shaped to receive the upper forearm, hand and thumb, respectively, of the individual. A longitudinal opening bifurcates the upper side of the body. The size of the opening is adjusted with locking straps to permit the device to be easily slipped on and off.

The forearm portion has a bulge to accommodate the distal ulnar prominence. Near the open end of the forearm portion, the top and bottom walls are flat to prevent rotation of an individual's forearm within. The hand portion angles upwardly from the forearm portion so that the wrist is held in an extended position, i.e., cocked upward, which is important for proper immobilization of navicular fractures.

The thumb portion extends at an angle from the hand portion so that the thumb is held in apposition, i.e., extended away from the hand. This is important to permit the individual to use the thumb while wearing the device.

An opening, whose size is adjustable with a strap, extends through a side wall of the thumb portion. Thus, the diameter of the thumb portion can be controlled simply by tightening or loosening the strap. This not only allows easy insertion and removal of the thumb, but also provides for secure immobilization with the adjustability to loosen the device if the thumb swells or tighten the device if swelling subsides.

The device is easily and inexpensively manufactured due to the unitary molded body which has no padding lining its interior. This lack of padding allows the device to more securely immobilize the patient's thumb, hand and wrist and also allows the device to be easily custom fit by trimming it with a cutting implement.

These and other advantages will be amplified in the following discussion which makes reference to the accompanying drawings in which.

DETAILED DESCRIPTION OF THE PREFERRED EMBODIMENT

Figure 1:
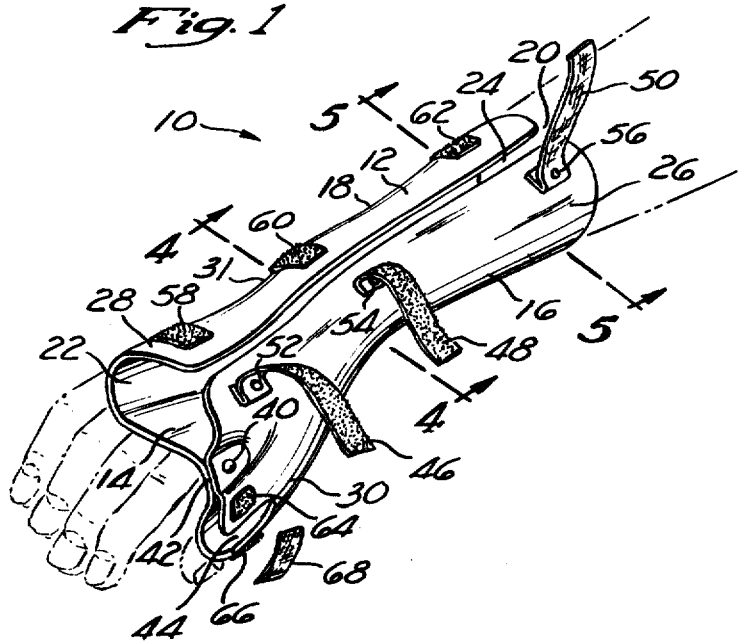
FIG. 1 is a perspective view of the thumb spica device illustrating its method of use on a patient's arm (shown in phantom)
Figure 2:
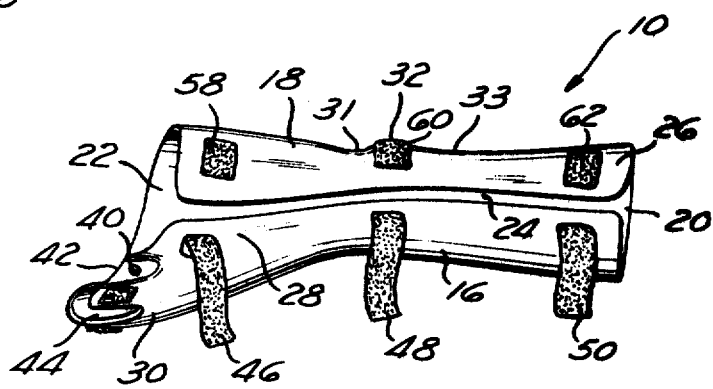
FIG. 2 is a top view of the thumb spica.

Referring to FIGS. 1-2, a device 10 is shown having elongate upper and lower walls 12,14 which are integrally joined by curved left and right side walls 16,18 to form a tubular shell with an open end 20 for the patient's forearm and an open end 22 for the patient's hand.

A narrow longitudinal opening 24 bifurcates the upper wall 12 and extends the length of the device 10.

The walls 12,14,16,18 are formed of a semi-rigid material which is sufficiently rigid to immobilize a patient's thumb, hand and wrist, but is sufficiently pliable to permit it to be easily slipped on and off the patient as will be hereinafter described. A material found satisfactory is polyethylene.

Although the device 10 is an integral unit, it can be conceptualized as having forearm, hand and thumb portions 26,28,30 which are shaped to cover the forearm, hand and thumb, respectively, of the patient.

Unlike some prior devices, the interior of the walls 12,14,16,18 is not lined with a cushioned material. This lack of padding allows the walls 12,14,16,18 to fit snugly against the patient's skin providing for more secure immobilization. Moreover, the device 10 can be readily custom fit for a particular patient by trimming the shell with a cutting implement. Specifically, the length of the hand and thumb portions 28,30 can be cut to the length required by the individual with ordinary scissors. Moreover, if any harmful pressure points develop due to a particular bone prominance of the individual, a cast saw can be used to cut into the shell to relieve the pressure.

The forearm portion 26 is a generally elongate tube. As best shown in FIG. 2, the right side wall 18 has a first indentation 31 which is located about at the junction between the forearm portion 26 and the hand portion 28 and a second indentation 33 laterally spaced from the first indentation 31 about an inch toward the forearm opening 20. The indentations 31,33 form an area 32, which bulges outward and is important because it is shaped to accommodate the distal ulnar prominence of the patient. This prominence is the protrusion of the ulnar bone near the wrist on the upper side of the forearm opposite the thumb. The remainder of the forearm portion 26 has a smaller diameter allowing for a tight fit around the patient's arm. The bulging area 32, therefore, permits a tight fit and prevents any harmful compression of the individual's wrist area.

Figure 4:
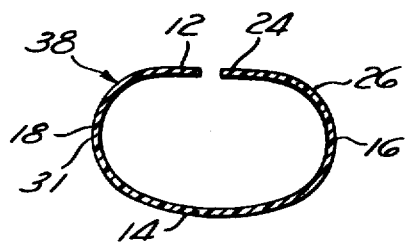
FIG. 4 is a sectional view taken through line 4—4 of FIG. 1.
Figure 5:
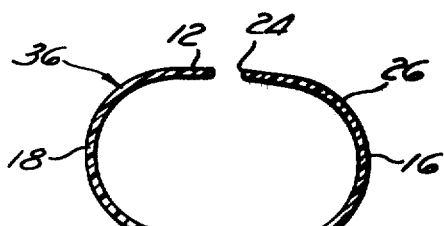
FIG. 5 is a sectional view taken through line 5—5 of FIG. 1.

FIGS. 4-5 show the cross section of the forearm portion 26 at two areas along its length. Referring to FIG. 5, a sectional view of the forearm portion 26 is shown in a region 36 proximate to the open end 20. In this region 36 the upper wall 12 and the lower wall 14 are flat.

Referring to FIG. 4, a sectional view of the forearm portion 26 is shown in a region 38 located between the region 36 and the hand portion 28 and more particularly in the bulging area 32. In this region 38, the upper wall 12 is flat, but the lower wall 14 concavely curves into the side walls 16,18.

The flattening of the lower wall 14 in the region 36 is an important advantage because in combination with the flattened upper wall 12 it prevents the patient's forearm from rotating within the device 10. Flattening of the upper wall 12 alone, as in the region 38, is not sufficient to prevent rotation. The lower wall 14 is flat only in the region 36 since this region covers that portion of the patient's forearm which has more fat and muscle tissue. This is important because the bottom of the patient's forearm (unlike the top) is rounded and thus the flattening achieved through the region 36 compresses the forearm somewhat. The fat and muscle tissue prevents the flattening of the lower wall 14 in the region 36 from being harmful or uncomfortable.

As most clearly shown in FIG. 2, the left side wall 16 of the device 10 angles outward from the end of the forearm portion 26 to the end of the thumb portion 30 so that the hand portion 28 is wider than the forearm portion 26.

Figure 3:
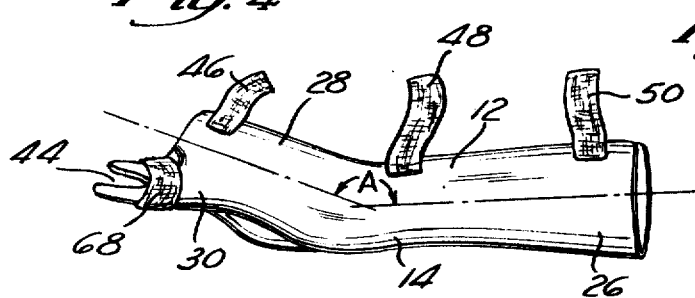
FIG. 3 is a side view of the thumb spica showing an angle A, made between the portions of the device which cover the hand and forearm.

As most clearly shown in FIG. 3, the upper and lower walls 12 and 14 in the hand portion 28 angle upward from the forearm portion 26. This angle is labeled A in FIG. 3. The purpose of this angle A is so that the wrist is held in an extended position when wearing the device. This means that the wrist is cocked upward which is important for proper immobilization and healing of the wrist, i.e., it permits fractures to heal in an approximated position. In the preferred embodiment the angle A is about 150°. It is satisfactory if the angle A is between about 170° and about 140°.

As shown in FIGS. 1-2, the thumb portion 30 extends beyond and away from the hand portion 28 which is important because the individual's thumb is held in apposition, i.e., in a position extended from the rest of the hand. This allows the individual to use the thumb while wearing the device 10.

The thumb portion is cylindrical and is separated from the hand portion 28 due to a rivet 40 which holds the upper and lower walls 12,14 together at a junction 42 between the hand and thumb portions 28,30.

A small opening 44 extends from the end of the thumb section 30 a substantial portion of its length through the left side wall 16. In the relaxed state of the polyethylene the opening 44 is about ⅛ inch in width.

The purpose and function of the opening 44 will be discussed hereinafter.

Referring to FIGS. 1-2, three straps 46,48,50 are laterally spaced along the length of the upper wall 12 and are secured to the left side of the opening 24 by rivets 52,54,56. The lower side of the straps 46,48,50 is fibrous. Patches 58,60,62 are glued on the right side of the opening 24, opposite straps 46,48,50, respectively. The upper side of the patches 58,60,62 is roughened. An example of a suitable material is that sold under the trademark Velcro ®. When the fibrous underside of the straps 46,48,50 is brought into contact with the roughened upper side of the patches 58,60,62 a lock is effected, as is well known. It should be understood that although Velcro ® has been found most satisfactory, other locking mechanisms such as buttons and buckles could be used.

Thumb patches 64,66 having roughened upper sides, are glued in opposing relation on opposite side of the opening 44. A strap 68 which is not affixed to the device 10 has a fibrous lower surface, e.g., Velcro ® material, for effecting a lock with the patches 64,66.

To employ the device all straps are disengaged from the patches. The patient's hand is inserted into the open end 20 of the forearm section 26 and slid forward toward the thumb portion 30. This sliding action will expand the opening 24 to permit the device 10 to be easily and comfortably slipped on. This expansion is made possible by the cooperative action of the opening 24 and the flexibility of the semi-rigid material. Thus, the material is rigid enough to immobilize the patient's arm but pliable enough to permit the opening 24 to expand allowing the device to be easily slipped on and off.

The hand continues to slide forward with the thumb entering the thumb portion 30. The rivet 40 will eventually stop the forward sliding of the hand. As shown in FIG. 1, when properly in place, the thumb portion 30 covers all of the thumb except that portion above the knuckle and the hand section 28 covers all of the hand except the fingers.

The opening 44, in the thumb portion 30 permits the thumb portion 30 to be adjusted in diameter. First, it allows the thumb portion 30 to expand upon entry of the thumb. Next, by applying the strap 68 to the patches 64,66 and pulling it across the opening 44 the opening 44 can be narrowed, thereby tightening the thumb portion 30 around the thumb. This provides for secure immobilization. Moreover, if the thumb should swell after fitting the device 10, the strap 68 can be loosened. Upon removal of the thumb from the thumb portion 30, the strap 68 is disengaged from one of the patches 64,66 to permit easy removal of the thumb.

When the device 10 is removed, the straps 46,48,50 are released from the patches 58,60,62, so that the forearm and hand portions 26,28 can expand in diameter permitting easy removal.

I claim:

1. A device for securely immobilizing an individual's wrist, hand and thumb for treatment of injuries to the wrist, hand and thumb, comprising:

an open ended integral body formed into a shell of semi-rigid material and having forearm, hand and thumb portions shaped to accommodate and immobilize an individual's forearm, hand and thumb, respectively, said body having means for permitting it to be easily slipped on and off the individual, said thumb portion having means for adjusting its size allowing the thumb portion to expand upon swelling or entry of the individual's thumb into said thumb portion and for tightening around the thumb after entry of the thumb to provide secure immobilization, said forearm portion having a bulge for accommodating an individual's distal ulnar prominence to permit the forearm portion to fit tightly against and immobilize the forearm without causing harmful compression of the wrist area, said forearm portion having flat areas in opposing relation to prevent rotation and provide secure immobiliation of an individual's forearm within the device and positioned to seat flush against the top and bottom of an individual's forearm in an area in which the forearm has substantial fat and muscle tissue.

2. A device for securely immobilizing an individual's wrist, hand and thumb for treatment of injuries to the wrist, hand and thumb, comprising:

a shell of semi-rigid material having forearm, wrist and thumb portions shaped to receive, substantially surround and immobilize an individual's forearm, wrist and thumb, respectively, said thumb portion being formed as a one-piece tubular member with said shell having an opening extending therethrough on one side, and means for adjusting the size of said opening to permit the opening to expand upon entry or removal of the thumb and to be tightened securely around the thumb to prevent movement of the thumb when the device is worn.

3. A device for immobilizing an individual's wrist, hand and thumb for treatment of injuries to the wrist, hand and thumb, comprising:

a shell of semi-rigid material having wrist, hand and thumb portions shaped to form a pair of substantially parallel tubes for receiving an individual's hand and thumb, respectively, said thumb portion having an opening which divides the thumb portion into two sections, means for pulling said thumb sections together to narrow said opening and tightly immobilize an individual's thumb within the thumb portion, and means for disengaging said pulling means to permit said opening to widen upon removal or swelling of the thumb.

4. The device of claim 3, wherein said pulling means is a strap engageable with both sections across said opening.

5. A device for immobilizing an individual's wrist for treatment of injuries to the wrist, comprising:

an open-ended shell of semi-rigid material having hand and forearm portions shaped to receive and securely immobilize an individual's hand and forearm respectively, said forearm portion having a widened region to accommodate an individual's distal ulnar prominence, said forearm portion having flat regions in opposing relation to prevent an individual's forearm from rotating therein.

6. A device for immobilizing an individual's wrist for treatment of injuries to the wrist, comprising:

an open-ended integral body formed into a shell of semi-rigid material, said body having forearm and hand portions sized to receive an individual's hand and forearm, and means for reducing the size of said portions to tighten said shell of semi-rigid material contiguously around the individual's hand and forearm and effect secure immobilization, said forearm portion having a bulging area to accommodate an individual's distal ulnar prominence to permit said forearm portion to fit tightly without causing harmful compression, and having flattened areas in opposing relation which seat flush against the upper and lower sides of the individual's forearm to prevent any rotation of the forearm when the shell is tightened.

7. A device for securely immobilizing an individual's forearm, wrist, hand and thumb for treatment of fractures and sprains to the upper forearm, wrist, hand and thumb, comprising:

an open-ended tubular shell of semi-rigid material having elongated upper and lower walls which are integrally joined by curved left and right side walls, said shell having a narrow longitudinal opening which bifurcates the upper wall and permits adjustment of said shell relative to the individual's forearm, wrist, hand and thumb to effect secure immobilization of the individual's upper forearm, wrist, hand and thumb, said shell comprising:

an elongated forearm portion having a bulge shaped to accommodate the individual's distal ulnar prominence to permit a tight fit of said shell to the individual's forearm and to prevent harmful compression of the individual's distal ulnar prominence.

8. A device as defined in claim 7 wherein said shell comprises:

an elongated forearm portion; and a hand portion having upper and lower walls which angle upward from the forearm portion to securely hold the individual's wrist in an upwardly cocked position to assure healing of fractures and sprains in the individual's wrist in an approximated position.

9. A device as defined in claim 7 wherein said shell comprises:

an elongated forearm portion;

a hand portion extending from the forearm portion; and a cylindrical thumb portion formed as one piece with and extending beyond and away from the hand portion and having an opening in a side wall to allow adjustment of said thumb portion to provide secure immobilization of the individual's thumb throughout various stages of healing of an injury to the individual's thumb.

10. A device as defined in claim 7 wherein said shell comprises:

an elongated forearm portion having a bulge shaped to accommodate the individual's distal ulnar prominence to permit a tight fit of said shell to the individual's forearm and to prevent harmful compression of the individual's distal ulnar prominence;

a hand portion having upper and lower walls which angle upward from the forearm portion to securely hold the individual's wrist in an upward cocked position to assure healing of fractures and sprains in the individual's wrist in an approximated position; and a cylindrical thumb portion extending beyond and away from the hand portion and having an opening in a side wall to allow adjustment of said thumb portion to provide secure immobilization of the individual's thumb throughout various stages of healing of an injury to the individual's thumb.

11. A device as defined in claim 7 or 10 wherein said forearm portion comprises:
   a first region proximate the individual's forearm having flat upper and lower walls which compress the individual's forearm fat and muscle tissue and prevent the individual's forearm from rotating within the device; and
   a second region proximate the individual's wrist having a flat upper wall and a lower wall which concavely curves into the side walls.

12. A device as defined in claim 8 or 10 wherein said hand portion is cocked upward relative to the forearm portion at an angle of between 140° and 160°.

13. A device as defined in claim 9 or 10 wherein said thumb portion includes:
   a rivet holding the upper and lower walls together between the hand the the thumb portions to separate the thumb portion from the hand portion; and
   means for adjusting the degree of immobilization of the individual's thumb by closing the opening in the side wall to (i) provide the smallest degree of immobilization to permit movement and use of a non-injured thumb, and (ii) provide the greatest degree of immobilization to prevent movement of an injured thumb.

* * * * *